(12) United States Patent
Wu

(10) Patent No.: US 10,161,856 B1
(45) Date of Patent: Dec. 25, 2018

(54) MAGNETO-OPTICAL BIO-DETECTION DEVICES HAVING HIGH SENSITIVITY

(71) Applicant: Ping-Chieh Wu, Taipei (TW)

(72) Inventor: Ping-Chieh Wu, Taipei (TW)

(*) Notice: Subject to any disclaimer, the term of this patent is extended or adjusted under 35 U.S.C. 154(b) by 0 days.

(21) Appl. No.: 15/874,935

(22) Filed: Jan. 19, 2018

(51) Int. Cl.
| | |
|---|---|
| *G01N 21/17* | (2006.01) |
| *G01N 15/06* | (2006.01) |
| *G01N 33/543* | (2006.01) |
| *G01N 35/00* | (2006.01) |
| *G01N 33/12* | (2006.01) |
| *G01R 33/12* | (2006.01) |

(52) U.S. Cl.
CPC ..... *G01N 21/1717* (2013.01); *G01N 15/0656* (2013.01); *G01N 33/54326* (2013.01); *G01N 35/0098* (2013.01); *G01R 33/1269* (2013.01); *G01N 2021/1727* (2013.01)

(58) Field of Classification Search
CPC ............... G01R 33/12; G01R 33/1269; G01R 33/1276; G01N 21/1717; G01N 2021/1727; G01N 27/745; G01N 33/54326; G01N 15/0656; G01N 35/0098
See application file for complete search history.

(56) References Cited

U.S. PATENT DOCUMENTS

| | | | | | |
|---|---|---|---|---|---|
| 4,341,470 | A | * | 7/1982 | Parker | G01N 21/3103 356/307 |
| 4,725,140 | A | * | 2/1988 | Musha | G01N 21/21 356/336 |
| 4,801,552 | A | * | 1/1989 | Hoff | G01N 21/1717 422/82.09 |
| 5,110,727 | A | * | 5/1992 | Oberhardt | B01F 11/0045 |
| 5,252,493 | A | * | 10/1993 | Fujiwara | G01N 21/51 356/337 |
| 7,639,359 | B2 | | 12/2009 | Chung et al. | |
| 9,075,052 | B2 | * | 7/2015 | Schleipen | G01N 21/47 |
| 9,103,824 | B2 | * | 8/2015 | Ovsyanko | G01N 27/745 |
| 9,574,988 | B2 | * | 2/2017 | Donner | G01N 15/1459 |
| 9,784,735 | B2 | * | 10/2017 | Donolato | G01N 33/54333 |
| 9,784,736 | B2 | * | 10/2017 | Donolato | G01N 33/54313 |

* cited by examiner

*Primary Examiner* — Gordon J Stock, Jr.
(74) *Attorney, Agent, or Firm* — WPAT, PC

(57) ABSTRACT

A magneto-optical bio-detection device including: a sample cell, a coil, a magnetic core, a light source and a light detection unit. The sample cell is filled with a solution containing a detection object and a magnetic biosensor capable of combining with the detection object to form a magnetic cluster. The coil is used for producing an oscillating magnetic field. The magnetic core has a guide portion, and an upper magnetic pole and a lower magnetic pole located at both ends of the guide portion; on a cross section orthogonal to the oscillating magnetic field, a cross-sectional area of the upper magnetic pole is less than a cross-sectional area of the guide portion. The light source is used for emitting light rays to penetrate the sample cell. The light detection unit is used for receiving the light rays that penetrated the sample cell to produce a detection signal.

10 Claims, 11 Drawing Sheets

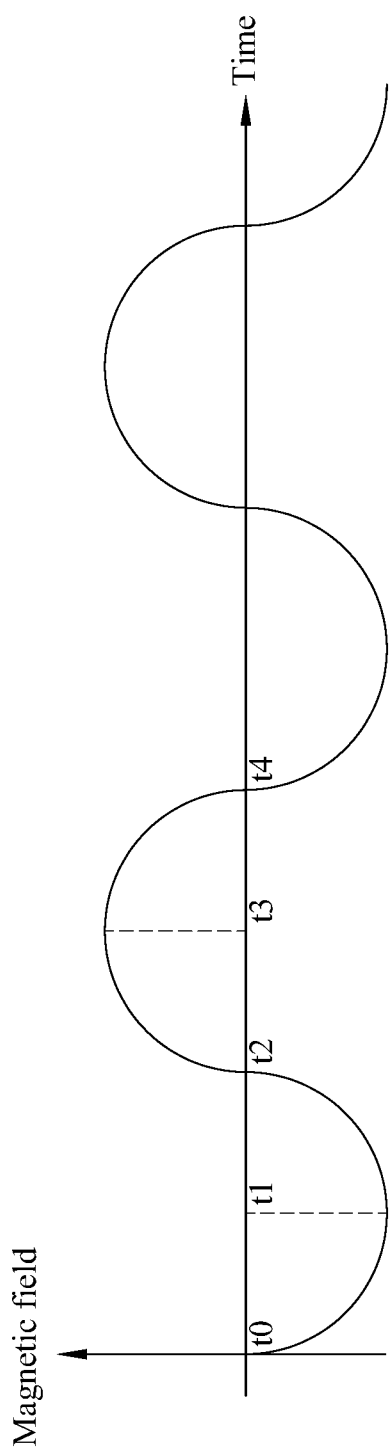

MAGNETO-OPTICAL BIO-DETECTION DEVICES HAVING HIGH SENSITIVITY

BACKGROUND OF THE INVENTION

1. Field of the Invention

The present application relates to a detection device, especially to a magneto-optical bio-detection device having high sensitivity.

2. The Prior Arts

In biological detecting technology, when a user utilizes a conventional absorption photometry to detect a detection object of trace amount, he can increase intensity of light rays to allow a light detection unit output a larger signal; however, the light rays of intensity increased will cause output signal saturation of the light detection unit, so that the detection result cannot be interpreted; therefore, the problem of the output signal saturation constrains the detection limit of the absorption photometry. Currently, a magneto-optical bio-detection device can obviate the problem of the output signal saturation of the light detection unit, and it can use light rays of high intensity to detect the detection object of an amount lower than the detection limit of the absorption photometry.

U.S. Pat. No. 7,639,359 discloses a magneto-optical bio-detection device, which uses magnetic force to allow a magnetic biosensor rotate in sample cell and combine with a detection object to form a magnetic cluster, uses laser light rays to penetrate the sample cell to produce light ray change caused by the rotation of the magnetic cluster, uses a light detection unit to receive the light ray change to produce a rotation track signal of the magnetic cluster, and uses a lock-in amplifier to calculate an amount of the magnetic cluster according to the rotation track signal. However, the magneto-optical bio-detection device disclosed in U.S. Pat. No. 7,639,359 does not have a mechanism for enhancing the signal of the light detection unit, so that a better detection result on detecting the detection object of very small amount cannot be obtained.

SUMMARY OF THE INVENTION

For increasing the detection sensitivity of the current magneto-optical bio-detection technology, the present application provides a magneto-optical bio-detection device including: a sample cell, a coil, a magnetic core, a light source and a light detection unit. The sample cell is filled with a solution containing a detection object and a magnetic biosensor capable of combining with the detection object to form a magnetic cluster. The coil is disposed at a side extended along a horizontal direction of the sample cell, and used for producing an oscillating magnetic field. The magnetic core has a guide portion and an upper magnetic pole and a lower magnetic pole located at both ends of the guide portion, the guide portion runs through an interior of the coil, the upper magnetic pole and the lower magnetic pole are respectively disposed above and under the sample cell; on a cross section orthogonal to the oscillating magnetic field, a cross-sectional area of the upper magnetic pole is less than a cross-sectional area of the guide portion; the oscillating magnetic field concentrates the magnetic biosensor and the magnetic cluster within a region of the sample cell through the upper magnetic pole and the lower magnetic pole, and drives rotations of the magnetic biosensor and the magnetic cluster in the region. The light source is disposed above the sample cell, and used for emitting light rays to penetrate the sample cell. The light detection unit is disposed under the sample cell, and used for receiving the light rays that penetrated the sample cell to produce a detection signal.

In an embodiment, a relative magnetic permeability of the magnetic core is not less than 200.

In an embodiment, the cross-sectional area of the upper magnetic pole on the cross section orthogonal to the oscillating magnetic field is not greater than 3 mm$^2$.

In an embodiment, a wavelength of the light source is not greater than 650 nm.

In an embodiment, magnetic paths of the oscillating magnetic field penetrating the sample cell and a vertical direction of the sample cell are separated by an angle.

In an embodiment, light paths of the light rays penetrating the sample cell and a vertical direction of the sample cell are separated by an angle.

In an embodiment, the light detection unit produces the detection signal according to changes of the light rays caused by the rotations of the magnetic biosensor and the magnetic cluster.

In an embodiment, the detection signal includes a direct current signal and an alternating current signal of a frequency two times of a frequency of the oscillating magnetic field.

In an embodiment, the magneto-optical bio-detection device further includes an alternating current amplifier and a lock-in amplifier, after the alternating current amplifier received the detection signal, the alternating current amplifier filters out the direct current signal and amplifies the alternating current signal; the lock-in amplifier respectively produces amplitudes of the detection signals of the magnetic biosensor and the magnetic cluster according to the amplified alternating current signals.

In an embodiment, an amount of the detection object is proportional to the difference of the amplitudes of the detection signals of the magnetic biosensor and the magnetic cluster.

The magneto-optical bio-detection device of the present application increases the sensitivity of detecting the detection object of trace amount mainly by magnifying intensity of the light rays that penetrate a specific region of the sample cell. Magnifying the intensity of the light rays is implemented by guiding the oscillating magnetic field to the sample cell by using the magnetic poles with reduced cross-sectional area, and by concentrating the magnetic biosensor and the detection object to rotate in the specific region in the sample cell; due the area of the sample cell penetrated by the light rays is reduced, intensity of the light rays that penetrates the sample cell can be thus increased, and the increased intensity of the light rays may help detecting the detection object of trace amount.

In addition, in the magneto-optical bio-detection device of the present application, the oscillating magnetic field drives the rotations of the magnetic biosensor and the magnetic cluster, the rotations thereof causes the changes of the light rays that penetrates the sample cell; the light detection unit produces the detection signals, which include a direct current (DC) signal and an alternating current (AC) signal of a frequency two times of the frequency of the oscillating magnetic field, according to the changes of the light rays that penetrate the sample cell; the magneto-optical bio-detection device of the present application can further filter out the DC signal and magnify the AC signal with the AC amplifier, the Lock-in amplifier can calculate the amplitudes of the detection signals of the magnetic biosensor and the magnetic cluster according to the amplified alternating current signals; thereby, the detection limit can be greatly reduced to $1/10^2$ in compared with the current magneto-optical bio-detection technology.

BRIEF DESCRIPTION OF THE DRAWINGS

The present application can be understood in more detail by reading the subsequent detailed description in conjunction with the examples and references made to the accompanying drawings, in which:

FIG. 5A illustrates an oscillogram of the oscillating magnetic field in the magneto-optical bio-detection device of the present application.

DETAILED DESCRIPTION OF THE PREFERRED EMBODIMENTS

The present application may be embodied in various forms and the details of the preferred embodiments of the present application will be described in the subsequent content with reference to the accompanying drawings. The drawings (not to scale) show and depict only the preferred embodiments of the invention and shall not be considered as limitations to the scope of the present application. Modifications of the shape of the present application shall be considered to be within the spirit of the present application.

Figure 1A:
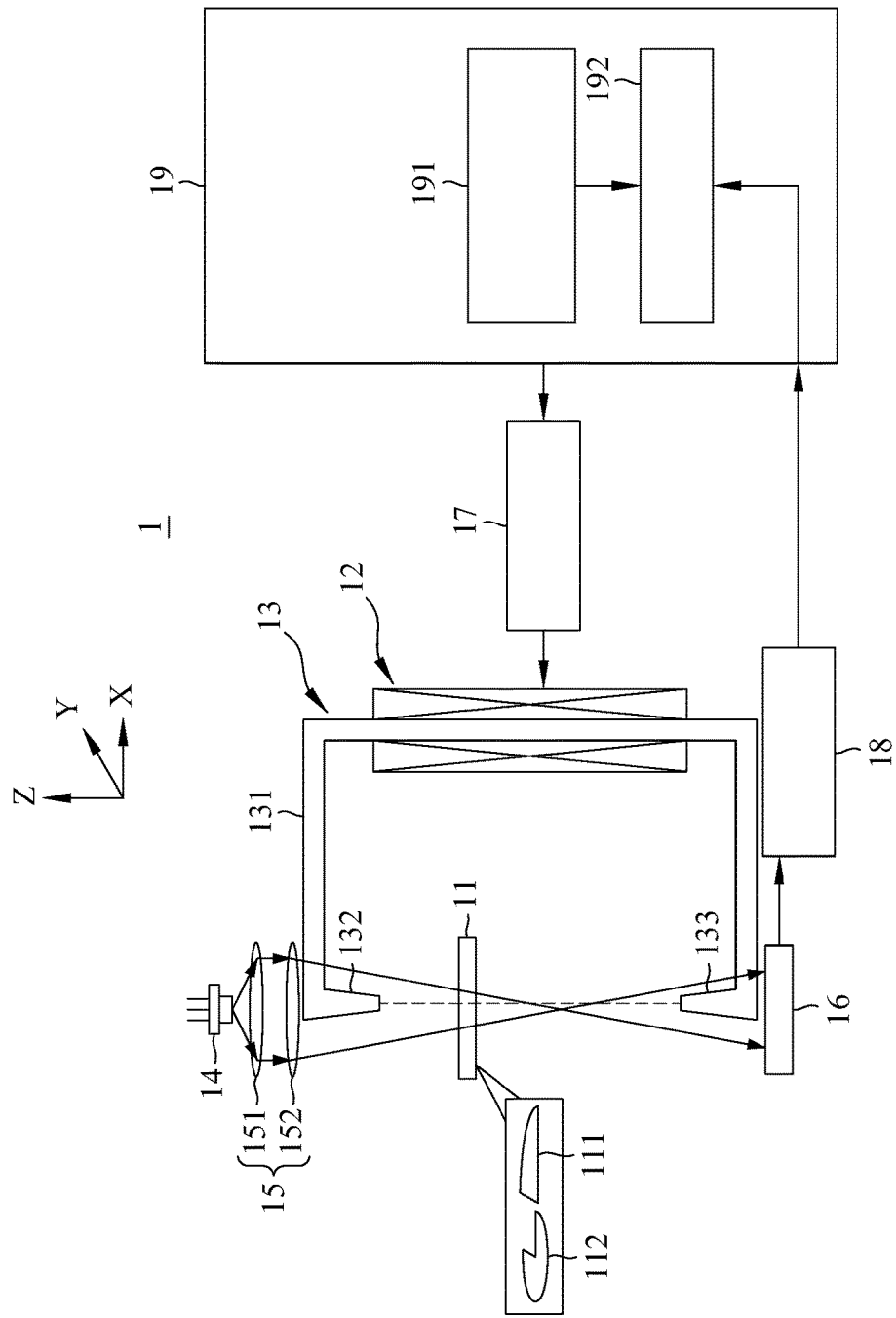
FIG. 1A schematically illustrates a structure of a magneto-optical bio-detection device according to a first embodiment of the present application, FIG. 1B schematically illustrates a structure of a magneto-optical bio-detection device according to a second embodiment of the present application, and FIG. 1C schematically illustrates a structure of a magneto-optical bio-detection device according to a third embodiment of the present application.

FIG. 1A schematically illustrates a structure of a magneto-optical bio-detection device according to a first embodiment of the present application. As shown in FIG. 1A, a magneto-optical bio-detection device 1 includes a sample cell 11, a coil 12, a magnetic core 13, a light source 14, a lens set 15, a light detection unit 16, a current amplifier 17, an alternating current (AC) amplifier 18 and a processing module 19. The sample cell 11 has a micro-flow channel (not shown) formed on a horizontal direction (as X-axis shown in FIG. 1A), the micro-flow channel is filled with a solution contains a detection object 111 and a magnetic biosensor 112, the magnetic biosensor 112 is consisting of a magnetic nanoparticle and a biosensor, a combination of the magnetic biosensor 112 and the detection object 111 has specificity to form a magnetic cluster. The coil 12 is disposed at a side extended along a horizontal direction of the sample cell 11, and used for producing an oscillating magnetic field. The magnetic core 13 has a guide portion 131, and an upper magnetic pole 132 and a lower magnetic pole 133 located at both ends of the guide portion 131, wherein the guide portion 131 runs through an interior of the coil 12 and extends to two opposite sides along a vertical direction (as Z-axis shown in FIG. 1A) of the sample cell 11, and the oscillating magnetic field penetrates the sample cell 11 through the upper magnetic pole 132 and the lower magnetic pole 133. The light source 14 is disposed above the upper magnetic pole 132 (oppositely to the sample cell 11), and used for emitting light rays of wavelength less than a specific value (e.g. 650 nm) to penetrate the sample cell 11. The lens set 15 is disposed between the light source 14 and the upper magnetic pole 132, and includes a collimating lens 151 and an objective lens 152. The light detection unit 16 is disposed under the lower magnetic pole 133 (oppositely to the sample cell 11), and used for receiving the light rays penetrated the sample cell 11 to produce a detection signal. The current amplifier 17 connects to the coil 12, and used for supplying current required for the coil 12 to produce the oscillating magnetic field. The AC amplifier 18 electrically connects to the light detection unit 16, and is used for processing the detection signal of the light detection unit 16. The processing module 19 connects to the current amplifier 17 and the AC amplifier 18, and includes a digital signal processor (DSP) 191 and a lock-in amplifier 192, and is used for controlling the current amplifier 17 and calculating an amount of the detection object 111 according to the signal output by the AC amplifier 18.

In the first embodiment, the upper magnetic pole 132 and the lower magnetic pole 133 of the magnetic core 13, the light source 14, the lens set 15 and the light detection unit 16 are disposed along the vertical direction (as Z-axis shown in FIG. 1A) of the sample cell 11, so that the oscillating magnetic field and the light rays penetrate the sample cell 11 substantially along the vertical direction thereof. In other embodiments, magnetic paths of the oscillating magnetic field and light paths of the light rays penetrating the sample cell can be designed to form an angle.

Figure 1B:
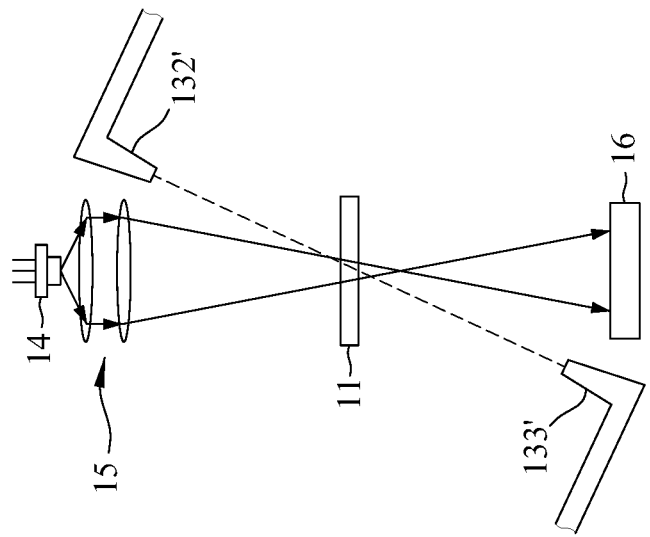

FIG. 1B schematically illustrates a structure of a magneto-optical bio-detection device according to a second embodiment of the present application. As shown in FIG. 1B, the upper magnetic pole 132 and the lower magnetic pole 133 of the magnetic core 13 are disposed along the vertical direction of the sample cell 11, to allow the oscillating magnetic field penetrate the vertical direction thereof; a light source 14' and a lens set 15' are disposed at a side extended along a parallel direction of the upper magnetic pole 132, a light detection unit 16' is disposed at a side extended along a parallel direction of the lower magnetic pole 133, so that the light paths of the light rays penetrating the sample cell 11 and the vertical direction of the sample cell 11 are separated by an angle.

Figure 1C:
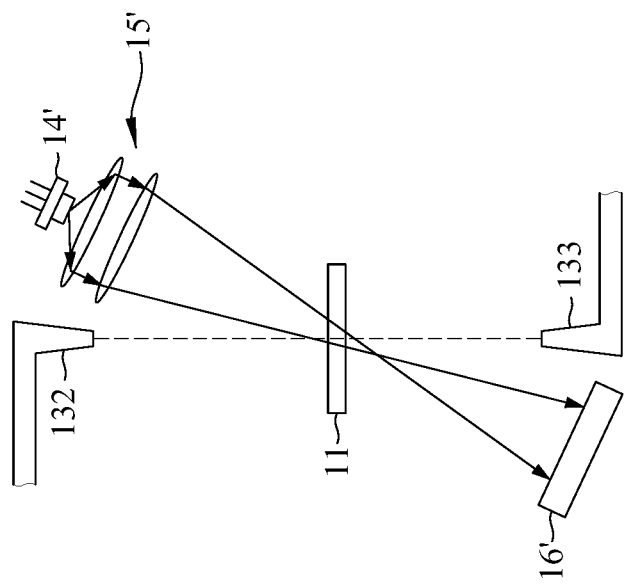

FIG. 1C schematically illustrates a structure of a magneto-optical bio-detection device according to a third embodiment of the present application. As shown in FIG. 1C, the light source 14, the lens set 15 and the light detection unit 16 are disposed along the vertical direction of the sample cell 11, to allow the light rays penetrate the sample cell 11 along the vertical direction thereof; a upper magnetic pole 132' of a magnetic core 13' is disposed at a side extended along a parallel direction of the light source 14, a lower magnetic pole 133' of a magnetic core 13' is disposed at a side extended along a parallel direction of the light detection unit 16, so that the magnetic paths of the oscillating magnetic field penetrating the sample cell 11 and the vertical direction of the sample cell 11 are separated by an angle.

Figure 2:
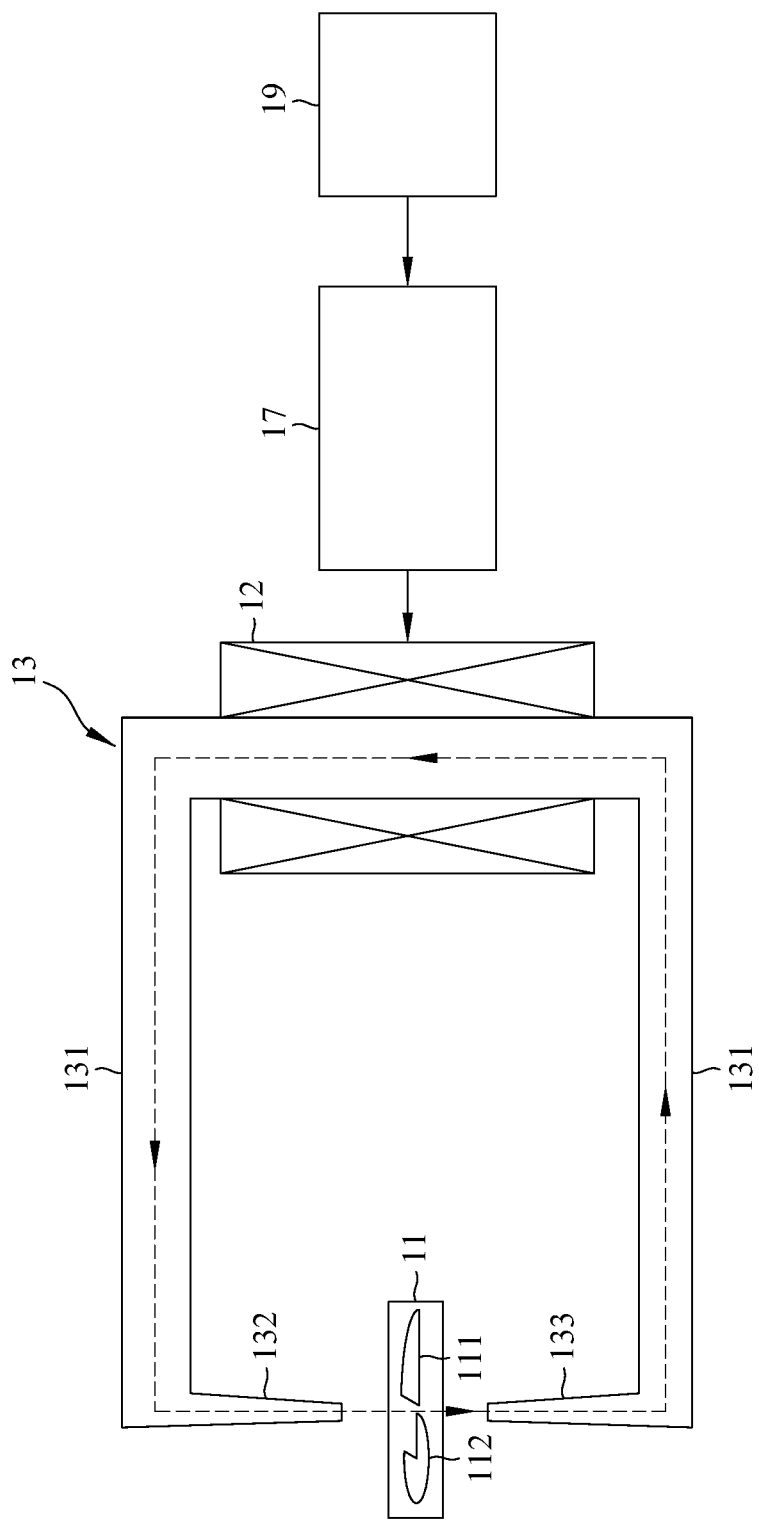
FIG. 2 schematically illustrates magnetic paths of the oscillating magnetic field of the magneto-optical bio-detection device of the present application.

FIG. 2 schematically illustrates the magnetic paths of the oscillating magnetic field of the magneto-optical bio-detection device according to the first embodiment. In the magneto-optical bio-detection device 1, the processing module 19 outputs a rotating wave signal to the current amplifier 17, the current amplifier 17 transforms the rotating wave signal to current, and transfers the current to the coil 12, to allow the coil 12 produce the oscillating magnetic field. The oscillating magnetic field passes through the magnetic core 13 and the sample cell 11 to form close magnetic paths (as the dashed line shown in FIG. 2); for obviate the rotations of magnetic biosensor 112 and the magnetic cluster be interfered with magnetic leakage flux of the coil 12, a distance between the sample cell 11 and the coil 12 is greater than a scope of the magnetic leakage flux of the coil 12. The magnetic core 13 is manufactured with materials of high inductivity (e.g. permalloy, ferrite material, etc.), the upper magnetic pole 132 and the lower magnetic pole 133 are respectively aligned to an upper side and a lower side of a specific region of the sample cell 11 on a vertical direction (as Z-axis shown in FIG. 2), on a cross section of the magnetic core 13 orthogonal to the magnetic paths of the oscillating magnetic field, cross-sectional areas of the upper magnetic pole and the lower magnetic pole 133 are less than a cross-sectional area of the guide portion 131, so that the magnetic paths of the oscillating magnetic field along the vertical direction of the sample cell 11 are concentrated within the scope of specific region of the sample cell 11, the magnetic biosensor 112 and the magnetic cluster (not shown) are driven by the oscillating magnetic field, and concentrated to rotate in the specific region of the sample cell 11. In this embodiment, a relative magnetic permeability of the magnetic core 12 is not less than 200, and the cross-sectional areas of the upper magnetic pole 132 and the lower magnetic pole 133 on the cross section orthogonal to the oscillating magnetic field are not greater than 3 mm$^2$.

Figure 3:
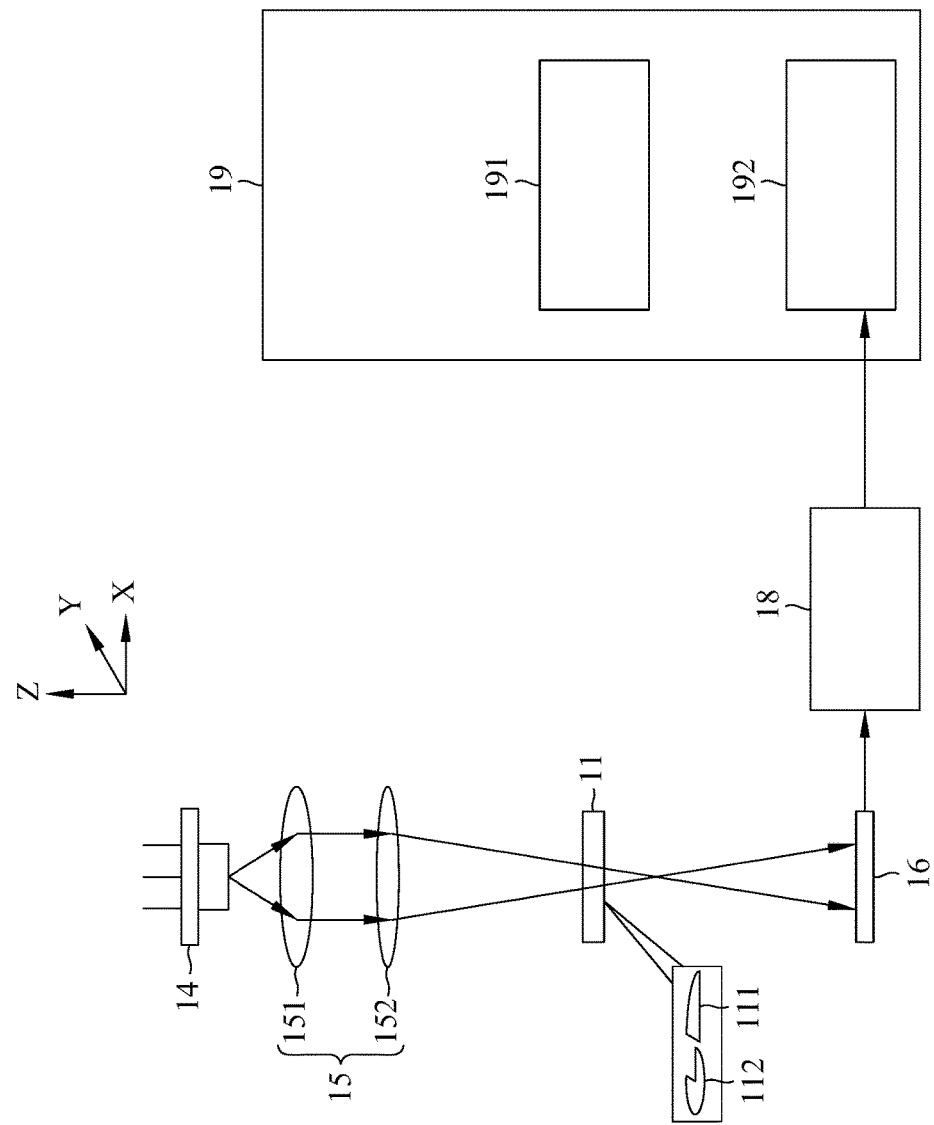
FIG. 3 schematically illustrates light paths of the light rays of the magneto-optical bio-detection device of the present application.

FIG. 3 schematically illustrates light paths of the light rays of the magneto-optical bio-detection device according to the first embodiment. As shown in FIG. 3, the light source 14 emits divergent light rays, the collimator lens 151 of the lens set 15 can transform the divergent light rays to parallel light rays, and the objective lens 152 can focus the parallel light rays to allow an irradiation area of the focusing light rays change with the light paths. Therefore, the irradiation area that the light rays irradiate the sample cell 11 can be set by adjusting a distance between the objective lens 152 and the sample cell 11. Although the upper magnetic pole 132 shields a portion of the light rays, most of the light rays can still pass through the lens set 15 and focus on the specific region of the sample cell 11. The light rays penetrated the specific region of the sample cell 11 occur changes due to the rotations of the magnetic biosensor 112 and the magnetic cluster (not shown), the light detection unit 16, for example a detection circuit containing photodiode, can receive the light rays penetrated the sample cell 11 to produce a detection signal, and the detection signal includes a direct current (DC) signal and an alternating current (AC) signal of a frequency two times of a frequency of the oscillating magnetic field.

To enhance gain of the detection signal of the light detection unit 16 can be reached by increasing light intensity of the light rays irradiating the sample cell 11, but the output saturation of the light detection unit 16 limits the light intensity of the light source 14. Suppose that the gain of the light detection unit 16 is designed to occur the output saturation on receiving the light rays penetrated an area (as X-Y plane shown in FIG. 3) of 9 mm$^2$ in the sample cell 11, on the conditions that the light intensity of the light source 14 is fixed and the magnetic biosensor 112 or the magnetic cluster uniformly distributed in the sample cell 11, if the area that the light rays penetrated the sample cell 11 were reduced from 9 mm$^2$ to 0.09 m$^2$ only by using the objective lens focusing the light rays, the light intensity of the light rays penetrated the specific region of the sample cell 11 were thus increased 100 times than the original light intensity, due an amount of the magnetic biosensor 112 or the magnetic cluster in 0.09 mm$^2$ were $1/100$ of an amount of the magnetic biosensor 112 or the magnetic cluster in 9 mm$^2$, the effect of increasing the light intensity would be counteracted by the factor of decreasing the amount of the magnetic biosensor 112 or the magnetic cluster, the detection signal of the light detection unit 16 would not change, and thus the detection sensitivity would not be enhanced.

According to the aforesaid conditions, the magneto-optical bio-detection device 1 of the present application utilizes the upper magnetic pole 132 and the lower magnetic pole 133 of the cross-sectional area reduced to guide the oscillating magnetic field to concentrate the area of the magnetic biosensor 112 or the magnetic cluster distributed in the sample cell 11 from 9 mm$^2$ to 0.09 mm$^2$, due the light intensity of the light rays penetrated the sample cell 11 is increased 100 times than the original light intensity, and the amount of the magnetic biosensor 112 or the magnetic cluster penetrated by the light rays are not changed, the intensity of the detection signal of the light detection unit 16 is increased 100 times than the original intensity, so that the detection sensitivity thereof is enhanced 100 times (i.e. the lowest detection amount is reduced to $1/100$ of the lowest detection amount of the current device).

Figure 4:
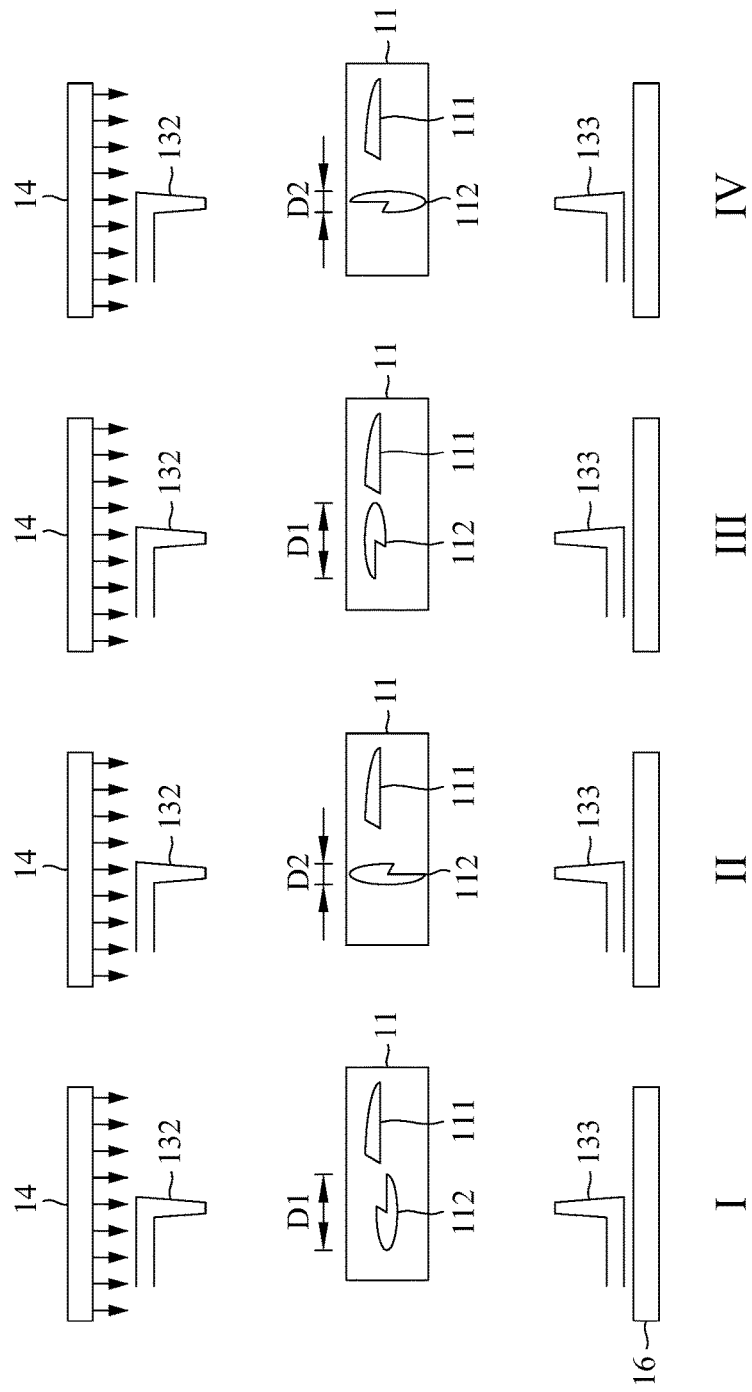
FIG. 4 schematically illustrates the rotation of the magnetic biosensor driven by the oscillating magnetic field in the magneto-optical bio-detection device of the present application.

FIG. 4 schematically illustrates the rotation of the magnetic biosensor driven by the oscillating magnetic field in the magneto-optical bio-detection device according to the first embodiment. As shown in FIG. 4, when the magnetic biosensor 112 not yet combines with the detection object 111, the upper magnetic pole 132 and the lower magnetic pole 133 guide the oscillating magnetic field to penetrate the specific region of the sample cell 11, the oscillating magnetic field drives the magnetic biosensor 112 rotating in an order of states I, II, III and IV, wherein an area D1 that the magnetic biosensor 112 of rotating to the state I or III shields the light rays penetrating the sample cell 11 is greater than an area D2 that the magnetic biosensor 112 of rotating to the state II or IV shields the light rays penetrating the sample cell 11; that is, when the magnetic biosensor 112 rotates to the state I or III, the intensity of the detection signal produced by the light detection unit 16 is smaller (the received light rays are less), when the magnetic biosensor 112 rotates to the state II or IV, the intensity of the detection signal produced by the light detection unit 16 is greater (the received light rays are more).

Figure 5B:
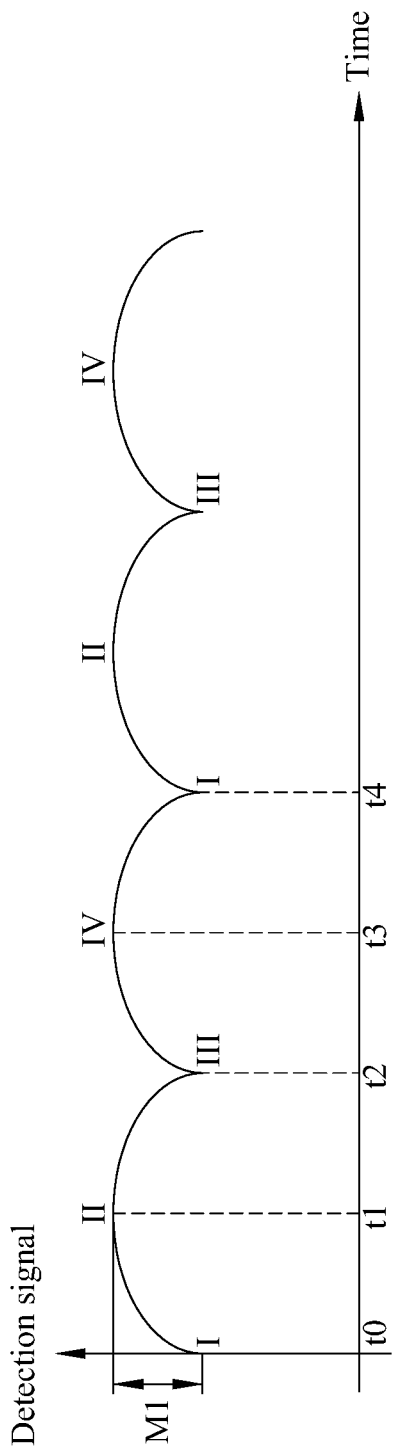
FIG. 5B illustrates an oscillogram of the detection signal of the light detection unit corresponding to the rotation of the magnetic biosensor.

FIG. 5A illustrates an oscillogram of the oscillating magnetic field in the magneto-optical bio-detection device of the present application, and FIG. 5B illustrates an oscillogram of the detection signal of the light detection unit corresponding to the rotation of the magnetic biosensor. A period of the oscillating magnetic field is t4-t0, the rotating states of the magnetic biosensor 112 (as shown in FIG. 4) corresponding to each the period of the oscillating magnetic field are described as follows: time at to, the magnetic biosensor 112 rotates to the state I; time at t1, the magnetic biosensor 112 rotates to the state II; time at t2, the magnetic biosensor 112 rotates to the state III; time at t3, the magnetic biosensor 112 rotates to the state IV; time at t4, the magnetic biosensor 112 rotates to the state I again. As shown in FIG. 5B, the detection signal output by light detection unit 16 is a combination of the AC signal and the DC signal, the frequency of the AC signal is two times of the frequency of the oscillating magnetic field, the intensities of the detection signals corresponding to the rotating states of the magnetic biosensor 112 are described as follows: time at to, the magnetic biosensor 112 rotates to the state I, the intensity of the detection signal reaches to the lowest value; time at t1, the magnetic biosensor 112 rotates to the state II, the intensity of the detection signal reaches to the highest value; time at t2, the magnetic biosensor 112 rotates to the state III, the intensity of the detection signal reaches to the lowest value again; time at t3, the magnetic biosensor 112 rotates to the state IV, the intensity of the detection signal reaches to the highest value again.

The detection signals of the light detection unit 16 are transferred to the AC amplifier 18, the AC amplifier 18 includes a DC signal filter circuit, an instrumentation amplifier and an analog-to-digital convertor (ADC), the DC signal filter circuit filters out the DC signal in the detection signal, the instrumentation amplifier magnifies the AC signal, the ADC obtains sampling data from the magnified AC signal and transfers the sampling data to the lock-in amplifier 192 of the processing module 19, the lock-in amplifier 192 calculates an amplitude M1 of the detection signal corresponding to the rotation of the magnetic biosensor 112 according to the sampling data.

Figure 6:
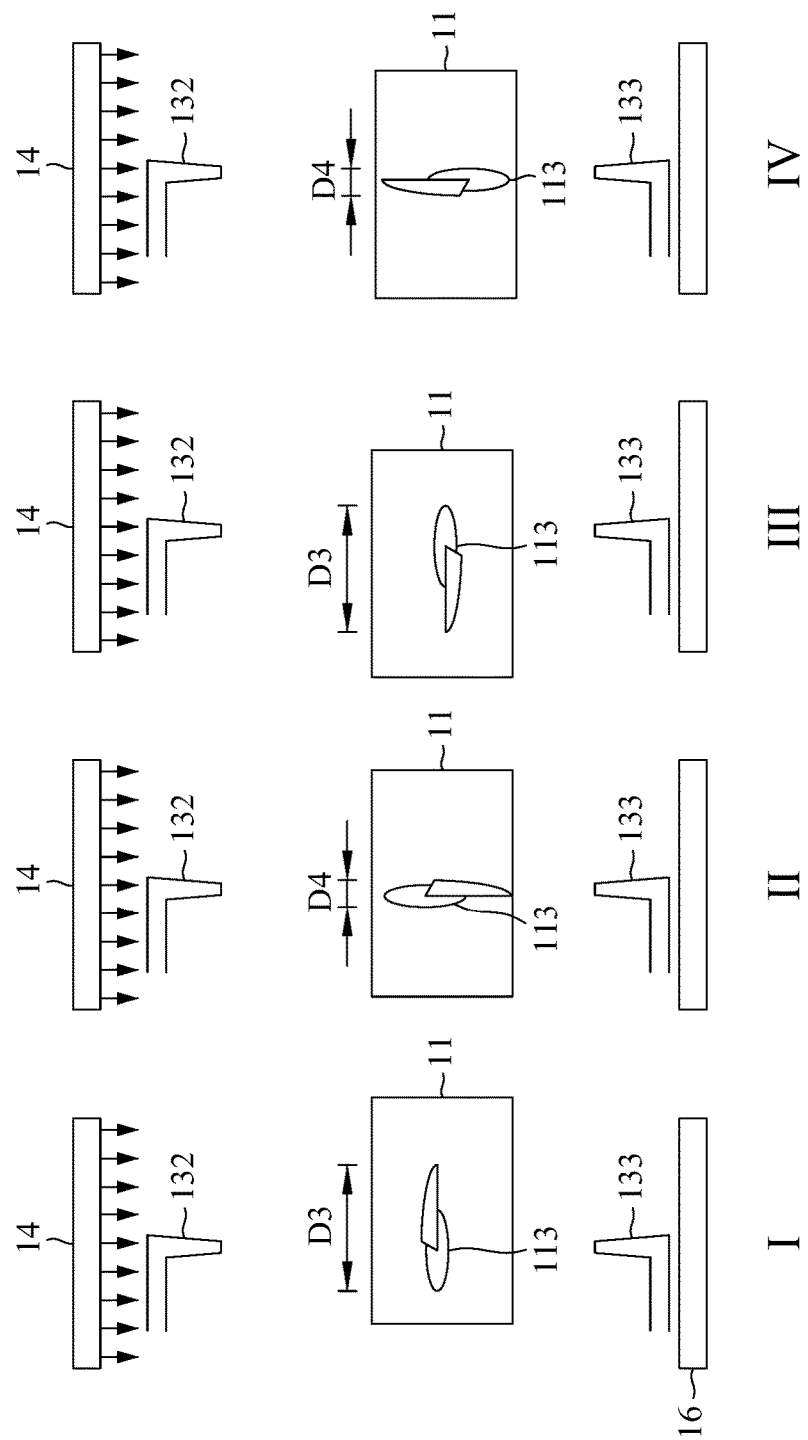
FIG. 6 schematically illustrates the rotation of the magnetic cluster driven by the oscillating magnetic field in the magneto-optical bio-detection device of the present application.

FIG. 6 schematically illustrates the rotation of the magnetic cluster driven by the oscillating magnetic field in the magneto-optical bio-detection device according to the first embodiment. As shown in FIG. 6, the upper magnetic pole 132 and the lower magnetic pole 133 guide the oscillating magnetic field to penetrate the specific region of the sample cell 11, the oscillating magnetic field allows the magnetic biosensor 112 combine with the detection object 111 to form the magnetic cluster 113 in the sample cell 11, and drives magnetic cluster 113 rotating in an order of states I, II, III and IV, wherein an area D3 that the magnetic cluster 113 of rotating to the state I or III shields the light rays penetrating the sample cell 11 is greater than the area D1 that the magnetic biosensor 112 of rotating to the state I or III shields the light rays penetrating the sample cell 11, an area D4 that the magnetic cluster 113 of rotating to the state II or IV shields the light rays penetrating the sample cell 11 is less that the area D2 that the magnetic biosensor 112 of rotating to the state II or IV shields the light rays penetrating the sample cell 11; that is, the intensity of the detection signal on the magnetic cluster 113 rotating to the state I or III is smaller than the intensity of the detection signal on the magnetic biosensor 112 rotating to the state I or III, the intensity of the detection signal on the magnetic cluster 113 rotating to the state II or IV is greater than the intensity of the detection signal on the magnetic biosensor 112 rotating to the state II or IV.

Figure 7A:
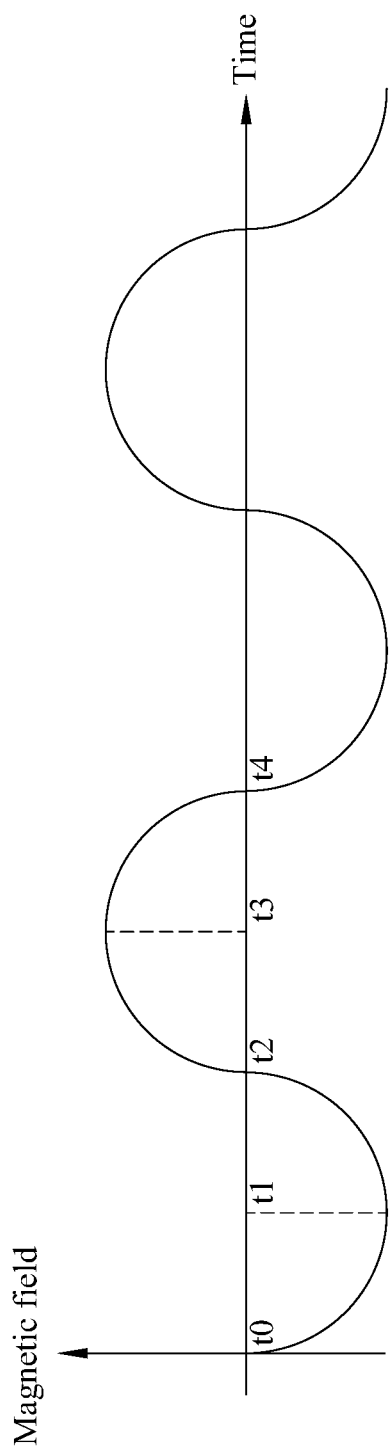
FIG. 7A illustrates an oscillogram of the oscillating magnetic field in the magneto-optical bio-detection device of the present application.
Figure 7B:
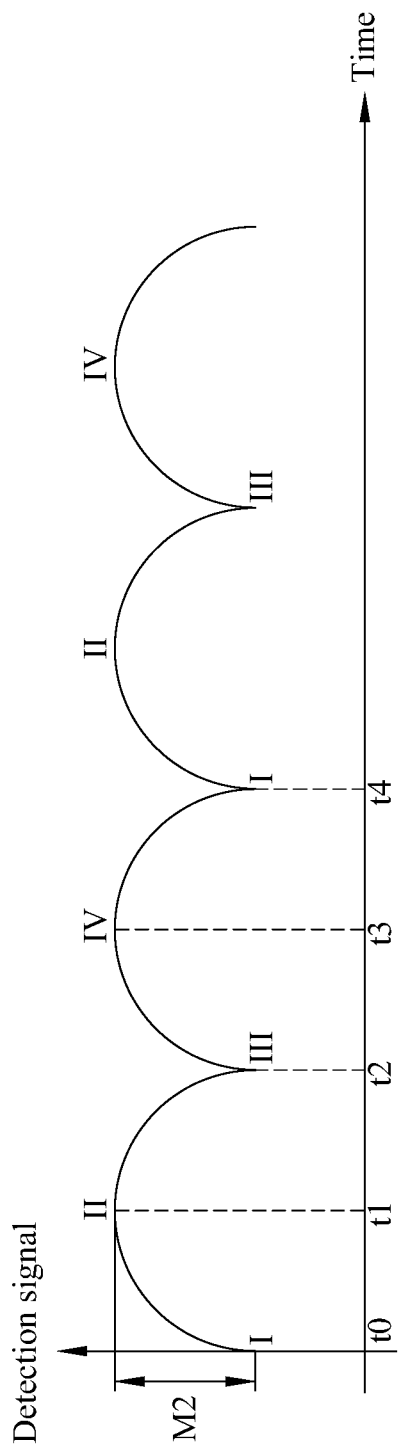
FIG. 7B illustrates an oscillogram of the detection signal of the light detection unit corresponding to the rotation of the magnetic cluster.

FIG. 7A illustrates an oscillogram of the oscillating magnetic field in the magneto-optical bio-detection device of the present application, and FIG. 7B illustrates an oscillogram of the detection signal of the light detection unit corresponding to the rotation of the magnetic cluster. A period of the oscillating magnetic field is t4-t0, the rotating states of the magnetic cluster 113 (as shown in FIG. 6) corresponding to each the period of the oscillating magnetic field are described as follows: time at t0, the magnetic cluster 113 rotates to the state I; time at t1, the magnetic cluster 113 rotates to the state II; time at t2, the magnetic cluster 113 rotates to the state III; time at t3, the magnetic cluster 113 rotates to the state IV; time at t4, the magnetic cluster 113 rotates to the state I again. As shown in FIG. 7B, the detection signal output by light detection unit 16 is a combination of the AC signal and the DC signal, the frequency of the AC signal is two times of the frequency of the oscillating magnetic field, the intensities of the detection signals corresponding to the rotating states of the magnetic cluster 113 are described as follows: time at t0, the magnetic cluster 113 rotates to the state I, the intensity of the detection signal reaches to the lowest value, and is lower than the intensity of the detection signal that the magnetic biosensor 112 rotates to the state I (as shown in FIG. 5B); time at t1, the magnetic cluster 113 rotates to the state II, the intensity of the detection signal reaches to the highest value, and is higher than the intensity of the detection signal that the magnetic biosensor 112 rotates to the state II (as shown in FIG. 5B); time at t2, the magnetic cluster 113 rotates to the state III, the intensity of the detection signal reaches to the lowest value again; time at t3, the magnetic cluster 113 rotates to the state IV, the intensity of the detection signal reaches to the highest value again.

The detection signals of the light detection unit 16 are transferred to the AC amplifier 18, the AC amplifier 18 filters out the DC signal in the detection signal, magnifies the AC signal, obtains sampling data from the magnified AC signal and transfers the sampling data to the lock-in amplifier 192 of the processing module 19, the lock-in amplifier 192 calculates an amplitude M2 of the detection signal corresponding to the rotation of the magnetic cluster 113 according to the sampling data.

Figure 8:
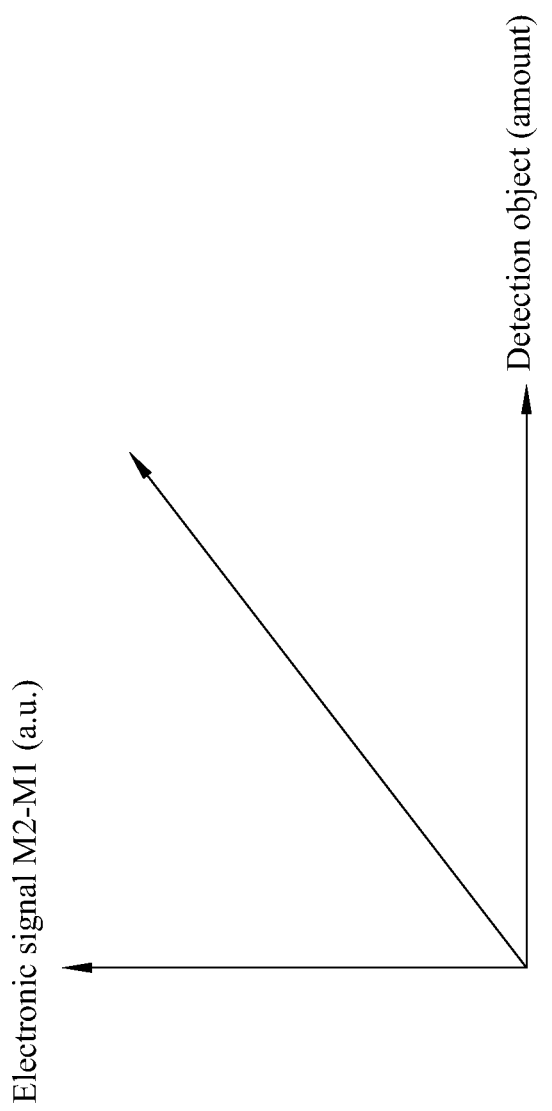
FIG. 8 is a diagram illustrating the relationship between the amount of the detection object and the amplitude difference of the detection signals obtained by the magneto-optical bio-detection device of the present application.

The digital signal processor 191 calculates an amount of the detection object 111 in the sample cell 11 according to the difference between the amplitudes M1 and M2 of the detection signals of the magnetic biosensor 112 and the magnetic cluster 113 produced by the lock-in amplifier 192. FIG. 8 is a diagram illustrating the relationship between the amount of the detection object and the amplitude difference of the detection signals obtained by the magneto-optical bio-detection device of the present application. A linear equation can be established based on known amounts and amplitude differences of standards of the detection object 111, and an amount of the detection object in an unknown sample can be calculated by interpolation.

In an embodiment, the detection object is biotinylated anti-streptavidin, the magnetic biosensor which has a specificity of combination with the detection object is streptavidin, the detection process includes following steps: in a step of preparing detection samples, adding magnetic nano-beads having a diameter of 80 nm into a solution containing streptavidin of 500 ug/mL, allowing the streptavidin cover the magnetic nano-beads to form a magnetic biosensor solution, respectively mixing the magnetic biosensor solution of 50 uL and two samples of 50 uL containing anti-streptavidin of concentrations from 30 pM to 500 pM, placing the mixed sample of 100 uL in the sample cell; in a step of detecting the magnetic biosensor, driving the magnetic biosensor with the oscillating magnetic field having an intensity of 2 mT, a cross-sectional area of the (upper and lower) magnetic pole of 3 mm² and an oscillating frequency of 20 Hz, irradiating the sample cell with a laser light source having a wavelength of 405 nm, a penetrating area of 6 mm² and an intensity of 1 mw, detecting changes of the light rays penetrating the sample cell containing the magnetic biosensor and the detection object; driving the magnetic biosensor in the sample cell move with the oscillating magnetic field of 80 mT, and allowing the detection object (streptavidin) combine with streptavidin of the magnetic biosensor to form the magnetic cluster, and irradiating the sample cell with the same laser light source, detecting changes of changes of the light rays penetrating the sample cell containing the magnetic cluster; calculating an amount of the detection object (streptavidin) in the sample cell according to the detection signals obtained by the two times of detecting the light ray changes.

In summary, in the magneto-optical bio-detection device of the present application, the oscillating magnetic field produced by the coil to the sample cell is guided by using the magnetic poles with reduced area, and the magnetic biosensor and the detection object are concentrated to rotate in the specific region in the sample cell; due the area of the sample cell penetrated by the light rays is reduced, intensity of the light rays that penetrates the sample cell can be thus increased, thereby, the detection limit can be greatly reduced to $1/10^2$ in compared with the current magneto-optical bio-detection technology.

Although the present application has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A magneto-optical bio-detection device, comprising:
    a sample cell, filled with a solution containing a detection object and a magnetic biosensor capable of combining with the detection object to form a magnetic cluster;
    a coil, disposed at a side extended along a horizontal direction of the sample cell, for producing an oscillating magnetic field;
    a magnetic core, having a guide portion, and an upper magnetic pole and a lower magnetic pole located at both ends of the guide portion, wherein the guide portion runs through an interior of the coil, the upper magnetic pole and the lower magnetic pole are respectively disposed above and under the sample cell, on a cross section orthogonal to the oscillating magnetic field, a cross-sectional area of the upper magnetic pole is less than a cross-sectional area of the guide portion, the oscillating magnetic field concentrates the magnetic biosensor and the magnetic cluster within a region of the sample cell through the upper magnetic pole and the lower magnetic pole, and the oscillating magnetic field drives rotations of the magnetic biosensor and the magnetic cluster in the region;
    a light source, disposed above the sample cell, for emitting light rays to penetrate the sample cell; and
    a light detection unit, disposed under the sample cell, for receiving the light rays that penetrated the sample cell to produce a detection signal.

2. The magneto-optical bio-detection device according to claim 1, wherein a relative magnetic permeability of the magnetic core is not less than 200.

3. The magneto-optical bio-detection device according to claim 1, wherein the cross-sectional area of upper magnetic pole on the cross section orthogonal to the oscillating magnetic field is not greater than 3 mm².

4. The magneto-optical bio-detection device according to claim 1, wherein a wavelength of the light source is not greater than 650 nm.

5. The magneto-optical bio-detection device according to claim 1, wherein magnetic paths of the oscillating magnetic field penetrating the sample cell and a vertical direction of the sample cell are separated by an angle.

6. The magneto-optical bio-detection device according to claim 1, wherein light paths of the light rays penetrating the sample cell and a vertical direction of the sample cell are separated by an angle.

7. The magneto-optical bio-detection device according to claim 1, wherein the light detection unit produces the detection signal according to changes of the light rays caused by the rotations of the magnetic biosensor and the magnetic cluster.

8. The magneto-optical bio-detection device according to claim 1, wherein the detection signal comprises a direct current signal and an alternating current signal of a frequency two times of a frequency of the oscillating magnetic field.

9. The magneto-optical bio-detection device according to claim 8, further comprising: an alternating current amplifier and a lock-in amplifier, after the alternating current amplifier receives the detection signal, the alternating current amplifier filters out the direct current signal and amplifies the alternating current signal; the lock-in amplifier respectively produces amplitudes of detection signals of the magnetic biosensor and the magnetic cluster according to amplified alternating current signals.

10. The magneto-optical bio-detection device according to claim 9, wherein an amount of the detection object is proportional to the difference of the amplitudes of the detection signals of the magnetic biosensor and the magnetic cluster.

* * * * *